US005695521A

United States Patent [19]
Anderhub

[11] Patent Number: 5,695,521
[45] Date of Patent: Dec. 9, 1997

[54] TUBULAR SHEATH PROTECTIVE INSERT

[75] Inventor: Otto E. Anderhub, Miami, Fla.

[73] Assignee: Symbiosis Corporation, Miami, Fla.

[21] Appl. No.: 725,328

[22] Filed: Oct. 1, 1996

[51] Int. Cl.$^6$ ............................................. A61B 17/28
[52] U.S. Cl. ................................................. 606/205; 606/206
[58] Field of Search ................................. 606/206, 205, 606/207, 208, 119, 122

[56] References Cited

U.S. PATENT DOCUMENTS

| | | | |
|---|---|---|---|
| 5,304,203 | 4/1994 | El-Mallawany et al. | 606/206 |
| 5,392,789 | 2/1995 | Slater et al. | 606/205 |

*Primary Examiner*—Michael Buiz
*Assistant Examiner*—Kevin Truong
*Attorney, Agent, or Firm*—David P. Gordon

[57] ABSTRACT

A surgical instrument having a protective distal insert is provided. The instrument generally comprises a tubular member containing a push rod which is axially movable within the tubular member by means of a proximal actuation handle. The tubular member is provided with a clevis at a distal end. End effectors provided with proximal tangs and cutting or gripping portions are coupled to the clevis and are further coupled to the push rod at the proximal tangs such that axial movement of the push rod is translated into rotational movement of the end effectors. Between the arms of the clevis a protective insert is provided. The protective insert is a relatively thin and elongate U-shaped member of Nylon, PTFE, or polyolefin, having a central portion provided with a central hole, and two arm portions. The push rod extends through the central hole and the insert is oriented such that arm portions are parallel to the push rod and are further aligned with the tangs of the end effectors, such that when the end effectors are opened and closed the tangs place their load on the arm portions of the insert. A thin insulative sheath extends over the distal end of the tubular member to the clevis. The protective insert protects the sheath from cracking and splitting caused by contact of the proximal tangs against the sheath.

13 Claims, 3 Drawing Sheets

TUBULAR SHEATH PROTECTIVE INSERT

BACKGROUND OF THE INVENTION

1. Field of the Invention

This invention relates broadly to surgical instruments. More particularly, this invention relates to endoscopic and laparoscopic surgical instruments having end effectors.

2. State of the Art

Endoscopic surgery is widely practiced throughout the world today and its acceptance is growing rapidly. In general, endoscopic/laparoscopic surgery involves one or more incisions made by trocars where trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the optical instrument in place in the trocar tube.

Various types of endoscopic surgical instruments are known in the art. These instruments generally comprise a metal tubular member containing a push rod which is axially movable within the tubular member by means of a proximal actuation handle. The tubular member is provided with a clevis at a distal end. End effectors having a proximal tang, a lateral bore, and a distal cutting or gripping portion, are coupled to the clevis at the lateral bores and are further coupled to the push rod at the tangs such that axial movement of the push rod is translated into rotational or pivotal movement of the end effectors. The cutting or gripping portions may take the form of scissors, grippers, cutting jaws, forceps, and the like. Extending over the tubular member from the proximal actuation handle to the clevis is a thin sheath, providing a smooth low friction surface for the tubular member from the proximal actuation handle to the clevis. On cautery-type instruments the sheath is typically FEP, providing an insulative cover for the metal tubular member of the instrument.

The distal end of a prior art instrument is shown in FIG. 1. As the end effectors 1a, 1b are rotated from an open position to a closed position, the tangs 2a, 2b of the end effectors tend to move outward beyond the diameter of the clevis 3 and place a load on the sheath 4 at diametrically opposed locations 5a, 5b. It is believed that the load causes high stress at the two opposed locations. Repeated rotation of the end effectors creates sufficient stress to crack and split the sheath at the locations 5a, 5b, reducing the insulative integrity of the sheath. In addition, sharp edges can result at the cracks and splits which arguably may cause injury on the patient in which the instrument is used and may hinder axial movement of the distal end of the instrument through an endoscope or trocar tube.

SUMMARY OF THE INVENTION

It is therefore an object of the invention to provide a means for preventing the sheath on the tube of an endoscopic or laparoscopic instrument from cracking and splitting.

It is another object of the invention to provide a means for distributing the load of the tangs of the end effectors of an endoscopic or laparoscopic instrument more evenly across the distal end of the sheath.

In accord with these objects which will be discussed in detail below, a surgical instrument having a protective distal insert is provided. The instrument generally comprises a tubular member containing a push rod which is axially movable within the tubular member by means of a proximal actuation handle. The tubular member is provided with a clevis at a distal end. A pair of end effectors each having a proximal tang and a distal portion are pivotally coupled to the clevis and are further coupled to the push rod at the proximal tangs. Axial movement of the push rod is translated into rotational movement of the end effectors. Between the arms of the clevis a protective insert is provided. The protective insert is a relatively thin and elongate U-shaped member of Nylon, Teflon, or polyolefin, having a central portion provided with a central hole, and two arm portions. The push rod extends through the central hole and the insert is oriented such that arm portions are parallel to the push rod and are further aligned with the tangs of the end effectors, such that when the end effectors are opened and closed the tangs engage the insert. A cautery connector is provided at the proximal actuation handle and coupled to the push rod. A thin insulative sheath extends over the tubular member from the proximal actuation handle to the clevis.

It will be appreciated that when the end effectors are rotated on the clevis, the tangs of the end effectors will exert a load against the insert, and the insert will distribute the load. As a result, the sheath is less likely to crack and split.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
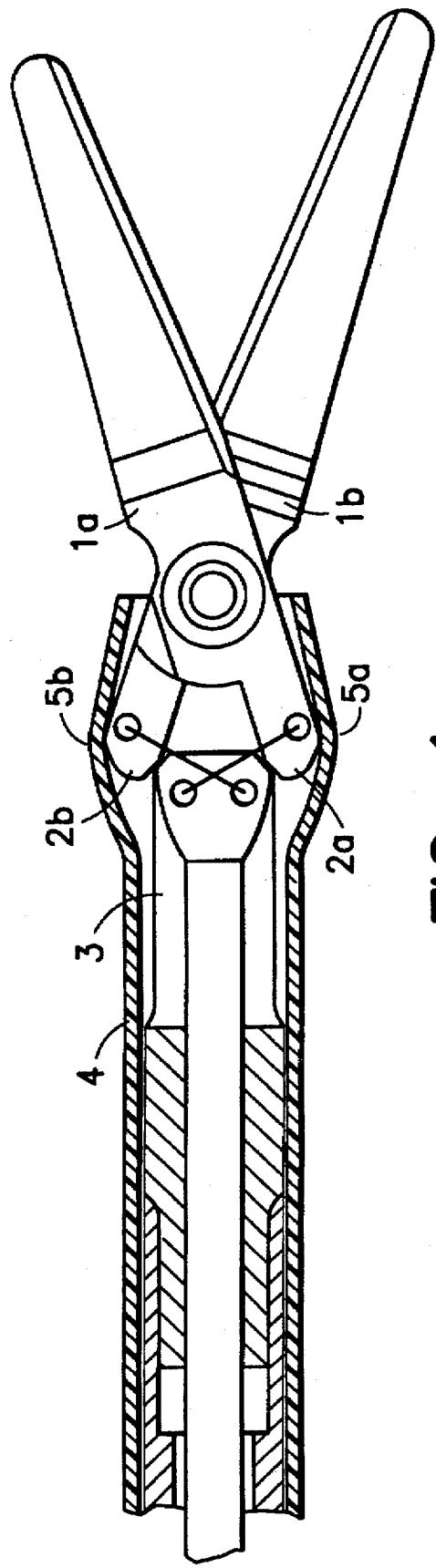
FIG. 1 is an enlarged broken side view in partial section of the distal end of a prior art surgical instrument.
Figure 2:
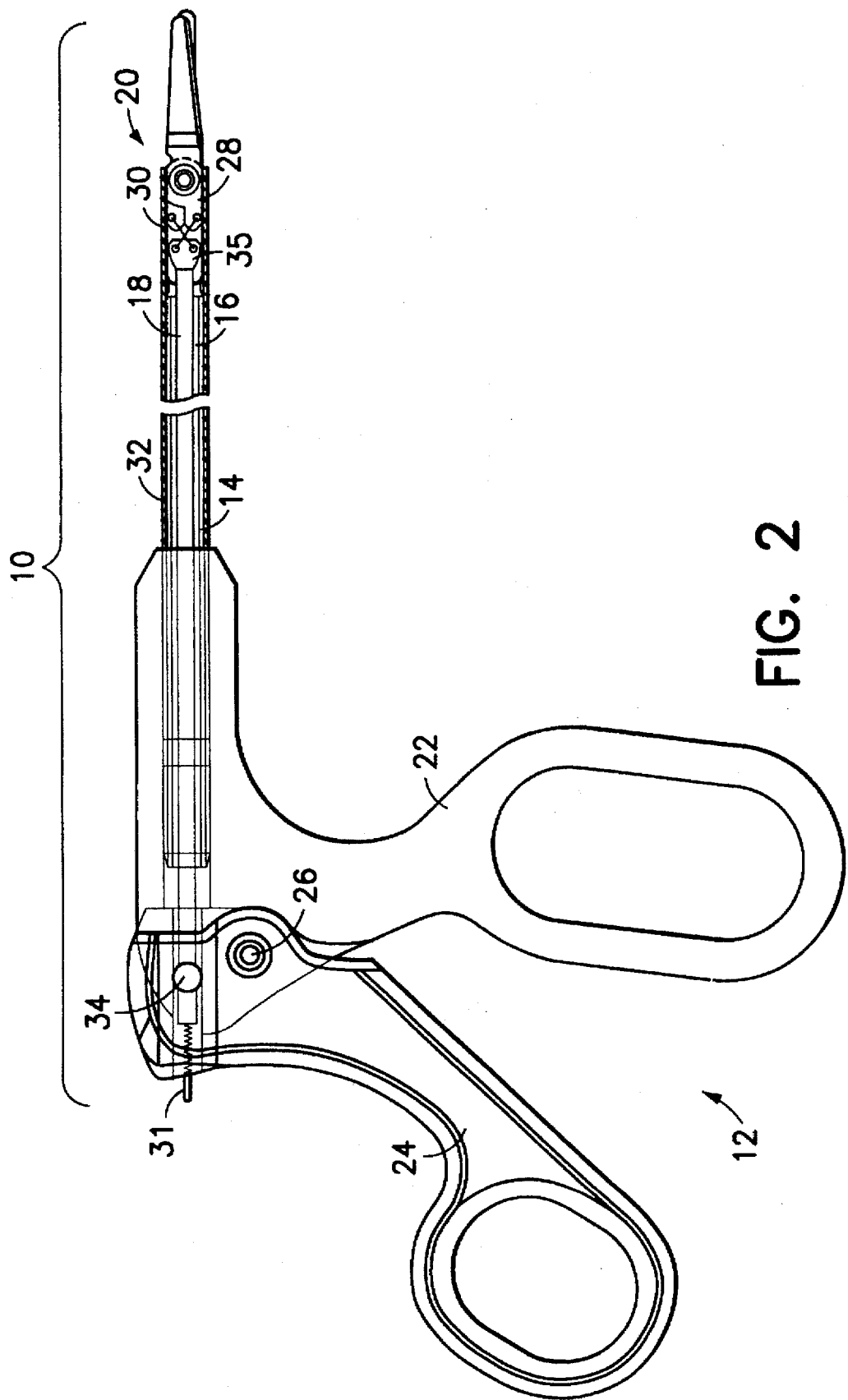
FIG. 2 is a broken side view in partial section of a surgical instrument of the invention.

Turning now to FIG. 2, a surgical instrument 10 is shown. The surgical instrument includes a proximal actuation handle assembly 12, a tubular member 14 having a lumen 16, a push rod 18 extending through the lumen, and an end effector assembly 20. The proximal actuation handle assembly 12 includes a fixed handle portion 22 and a lever 24 pivotally coupled to the fixed handle portion by a pivot pin 26. The tubular member is preferably a rigid tube, but may also be a flexible coil. The proximal end of the tubular member 14 is fixedly coupled to the handle portion 22. The distal end of the tubular member is provided with a clevis 28. As is described in more detail below, a protective insert 30 is provided between the arms of the clevis 28. An insulative sheath 32, preferably made of FEP, extends over the tubular member from the proximal actuation handle to the clevis 28, including covering the protective insert 30. A cautery connector 31 is provided on the proximal actuation handle and further coupled to the push rod 18. The push rod 18 is coupled at its proximal end to the lever 24 by a set screw 34 or other mechanism in a known manner and is provided at its distal end with a coupling means 35 for coupling to the end effector. It will be appreciated that the axial movement of the push rod 18 relative to the tubular member 14 is effected by pivotal movement of the lever 24 relative to the fixed handle portion 22.

Figure 3:
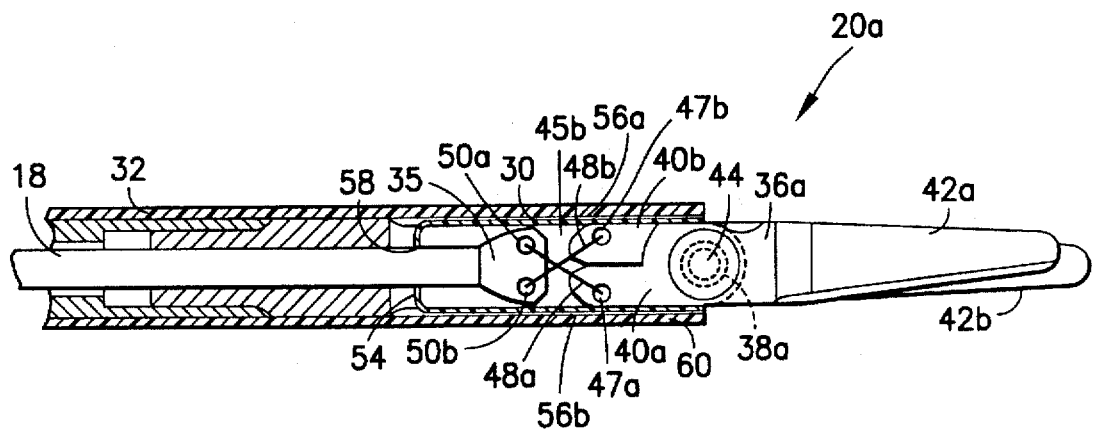
FIG. 3 is an enlarged broken side view in partial section of the distal end of the surgical instrument of FIG. 2 in which the end effectors are in a closed position.
Figure 4:
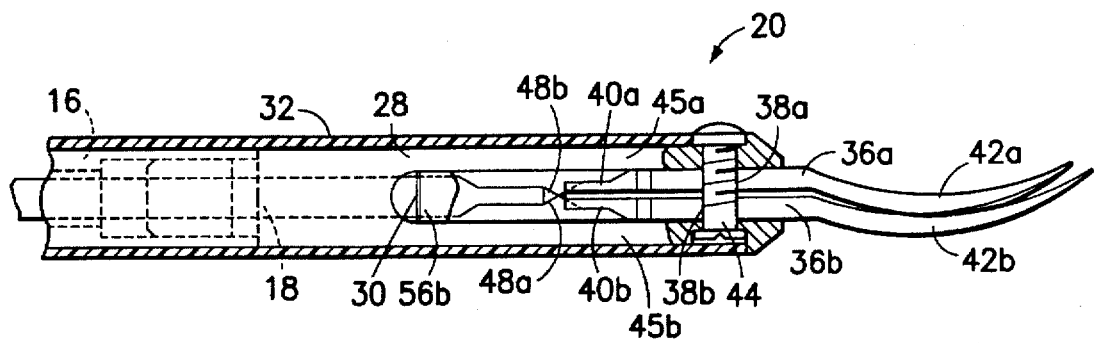
FIG. 4 is an enlarged broken bottom view in partial section of the distal end of the surgical instrument of FIG. 2 in which the end effectors are in a closed position.

Turning to FIGS. 3 and 4, the end effector assembly 20 is seen to generally include two end effectors 36a, 36b. The two end effectors 36a, 36b are each provided with a mounting bore 38a, 38b, a proximal tang 40a, 40b, and a blade portion 42a, 42b. The end effectors 36a, 36b are each rotatably mounted at the mounting bore 38a, 38b on an axle or clevis pin 44 between the arms 45a, 45b of the clevis 28. The proximal tang 40a, 40b of each end effector defines a hole 47a, 47b which is coupled by a link 48a, 48b to one of two holes 50a, 50b provided in diagonally opposed sides of the coupling means 35. The protective insert 30 is preferably a relatively thin U-shaped piece of Nylon, PTFE, or polyolefin. The protective insert 30 is provided with a central portion 54 and two elongate arm portions 56a, 56b. The central portion 54 defines a through hole 58, through which the push rod 18 extends, and the central portion 54 is further oriented perpendicular to the axle 44 and perpendicular to the push rod. As such, the arm portions 56a, 56b extend over the coupling means 35 and between the arms 45a, 45b of the clevis 28.

By way of an example, and not byway of any limitation on the scope of this invention, an insert for a 5 mm curved blade scissors may be dimensioned such that it has an approximately 1.000 inch total length, an approximately 0.096 inch width, and an approximately 0.069 inch diameter through hole. The thickness of the material used can be approximately 0.005 inches.

Figure 5:
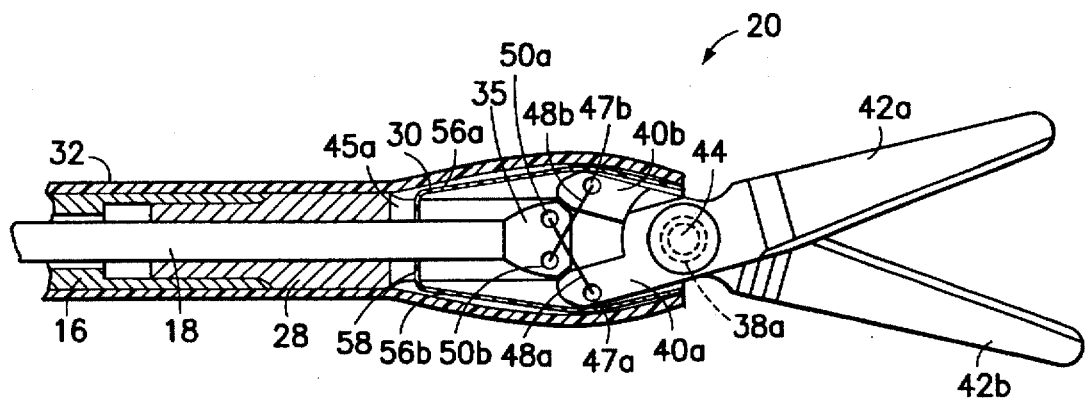
FIG. 5 is an enlarged broken side view in partial section of the distal end of the surgical instrument of FIG. 2 in which the end effectors are in an open position.

Referring to FIG. 2 through 5, it will be appreciated that axial movement of the push rod 18 relative to the tubular member 14 in a distal direction will result in the coupling means 35 moving closer to the axle 44, and thereby push the links 48a, 48b and proximal tangs 40a, 40b outward to effect an opening of the end effector 20, whereby the blade portions 42a, 42b scissor apart from each other (FIG. 5). Likewise, axial movement of the push rod relative to the tubular member in a proximal direction will effect a closing of the end effector (FIG. 4).

Referring to FIG. 5, the function of the insert 30 is particularly illustrated. As the tangs 40a, 40b are moved outward to scissor the blade portions 42a, 42b apart from each other, the tangs make point contact with the insert 30. The insert 30 distributes the load of the contact forces along the length and width of the insert. Consequently, as the insert further distributes the load to the sheath, the stress received at any one point along the sheath is reduced. In addition, the protective insert acts to reinforce the sheath at the locations of tang contact. By reducing the stress at any one point on the sheath and by reinforcing the sheath the likelihood of the sheath cracking and splitting is reduced.

There have been described and illustrated herein several embodiments of a surgical instrument having a protective insert. While particular embodiments of the invention have been described, it is not intended that the invention be limited thereto, as it is intended that the invention be as broad in scope as the art will allow and that the specification be read likewise. Thus, while a particular actuation handle has been disclosed, it will be appreciated that other actuation handles could likewise be used, such as a handle and spool arrangement, as disclosed in co-owned U.S. Pat. No. 5,133, 727, or a rack and pinion handle, as disclosed in co-owned U.S. Pat. No. 5,478,350, each of which is hereby incorporated herein in their entireties. Furthermore, while the described instrument is shown to have cautery ability, it will be appreciated that instruments not having cautery ability but supplied with a sheath may also take advantage of the protective insert, as described. Also, while Nylon, Teflon and polyolefin have been disclosed as preferred materials for the protective insert, it will be recognized that other materials which act to distribute the load of the tangs across a larger surface area may also be used. Moreover, while the instrument has been described and illustrated with respect to end effectors having curved scissors blade portions, it will be appreciated that end effectors having other scissors blades, forceps, clamps, or other useful configurations could be used as well. Furthermore, while the instrument has been described as having two rotatable end effectors, it will be understood that an instrument having a single rotatable end effector can be similarly used. In addition, while the clevis is shown distinct from the tubular member, it will be appreciated that the clevis may be integral with the tubular member. It will therefore be appreciated by those skilled in the art that yet other modifications could be made to the provided invention without deviating from its spirit and scope as so claimed.

We claim:

1. A surgical instrument, comprising:
 a) a tubular member having a proximal end and a distal end and defining an axis,
 b) a clevis having two arms provided at the distal end of said tubular member;
 c) a push rod having a proximal end and a distal end, said push rod extending through said tubular member;
 d) a proximal actuation handle coupled to said proximal end of said tubular member and said proximal end of said push rod such that actuation of said proximal actuation handle moves said push rod relative to said tubular member;
 e) a pair of end effectors mounted at said clevis, at least one of which is rotatable relative to the other, wherein each of said rotatable end effectors is provided with a proximal tang which is coupled to said distal end of said push rod, such that said proximal tang moves away from said axis of said tubular member and beyond said two arms of said clevis when said push rod is moved distally relative to said tubular member;
 f) a protective insert located at said distal end of said tubular member between said arms of said clevis; and
 g) a sheath extending over said tubular member from said actuation means to said clevis,
 wherein when said push rod is moved relative to said tubular member such that said end effectors are moved into an open position, said proximal tangs extends against said protective insert.

2. A surgical instrument according to claim 1, wherein:
 said protective insert is U-shaped.

3. A surgical instrument according to claim 2, wherein:
 said protective insert has a central portion and two elongate portions, said central portion defining a hole and being oriented substantially perpendicular to said axis of said tubular member and said two elongate portions extend substantially parallel to said tubular member, and
 said push rod extends through said hole.

4. An instrument according to claim 1, wherein:

said protective insert is made of one of Nylon, PTFE, and polyolefin.

5. A surgical instrument according to claim 1, wherein:

each of said pair of end effectors is rotatable relative to the other.

6. A surgical instrument according to claim 1, wherein:

said end effectors are provided with blade portions.

7. A surgical instrument according to claim 1, wherein:

said tubular member and said clevis are integral.

8. A surgical instrument according to claim 7, wherein:

said sheath is insulative.

9. A surgical instrument according to claim 1, further comprising:

h) cautery coupling means coupled to said proximal actuation handle.

10. A surgical instrument according to claim 9, wherein:

said sheath is made of FEP.

11. A protective insert for use with a surgical instrument having a tubular member provided with a proximal end and a distal end, and having a clevis at the distal end, a push rod provided with a proximal end and distal end extending through the tubular member, a proximal actuation handle coupled to the proximal end of the tubular member and the proximal end of the push rod for moving the push rod relative to the tubular member, a pair of rotatable end effectors provided with proximal tangs, the end effectors being rotatably mounted at the clevis and the proximal tangs being coupled to the distal end of the push rod, wherein the proximal tangs move in an arc when the end effectors are moved from a closed position into an open position, and a sheath over the tubular member from the proximal actuation handle extending to the distal end of the tubular member, said protective insert comprising:

a U-shaped member seated in the tubular member at the clevis and protecting the sheath from contact by the proximal tangs of the end effectors during rotation of the end effectors.

12. A protective insert according to claim 11, wherein:

said U-shaped member defines a central portion provided with a hole and two elongate portions, said central portion oriented substantially perpendicular to the push rod and said two elongate portions extending substantially parallel to the push rod, wherein the push rod extends through said hole and said elongate members extend along said push rod.

13. A protective insert according to claim 11, wherein:

said protective insert is made of one of Nylon, PTFE, and polyolefin.

\* \* \* \* \*